United States Patent
Girdhar et al.

(10) Patent No.: US 9,801,812 B1
(45) Date of Patent: *Oct. 31, 2017

(54) INJECTABLE NON-AQUEOUS COMPOSITIONS AND METHODS OF TREATING VASCULAR DISEASE

(71) Applicant: Covidien LP, Mansfield, MA (US)

(72) Inventors: Gaurav Girdhar, Ladera Ranch, CA (US); Xiaodong Ma, Acton, MA (US); Jennifer Makridakis, Mendon, MA (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/602,940

(22) Filed: May 23, 2017

Related U.S. Application Data

(63) Continuation of application No. 14/959,446, filed on Dec. 4, 2015, now Pat. No. 9,655,842.

(51) Int. Cl.
| | |
|---|---|
| A61K 9/00 | (2006.01) |
| A61K 31/734 | (2006.01) |
| A61K 47/10 | (2017.01) |
| A61K 47/14 | (2017.01) |
| A61K 31/722 | (2006.01) |

(52) U.S. Cl.
CPC .......... *A61K 9/0024* (2013.01); *A61K 31/722* (2013.01); *A61K 31/734* (2013.01); *A61K 47/10* (2013.01); *A61K 47/14* (2013.01)

(58) Field of Classification Search
None
See application file for complete search history.

(56) References Cited

U.S. PATENT DOCUMENTS

| | | |
|---|---|---|
| 5,614,204 A | 3/1997 | Cochrum |
| 6,344,488 B1 | 2/2002 | Chenite et al. |
| 6,818,018 B1 | 11/2004 | Sawhney |
| 8,481,695 B2 | 7/2013 | Melvik et al. |
| 8,530,632 B2 * | 9/2013 | Tijsma ............... A61K 9/19 536/20 |
| 8,809,521 B2 | 8/2014 | Melvik et al. |
| 9,655,842 B1 * | 5/2017 | Girdhar ............. A61K 9/0024 |
| 2002/0165337 A1 | 11/2002 | Wallace et al. |
| 2010/0028434 A1 | 2/2010 | Chenite et al. |
| 2011/0038938 A1 | 2/2011 | Ison et al. |
| 2012/0064136 A1 | 3/2012 | Baker, Jr. et al. |
| 2012/0100103 A1 | 4/2012 | Park et al. |
| 2014/0243395 A1 | 8/2014 | Rudoplh et al. |
| 2014/0277400 A1 | 9/2014 | Wainwright et al. |
| 2015/0111834 A1 | 4/2015 | Cheng et al. |
| 2015/0140344 A1 | 5/2015 | Ma et al. |

FOREIGN PATENT DOCUMENTS

WO  WO 2004098669 A1 * 11/2004 ........... A61K 9/0024

OTHER PUBLICATIONS

Saether et al. (Polyelectrolyte complex formation using alginate and chitosan, Carbohydrate polymers 74 (2008) 813-821).*
Saether et al. (Polyelectrolyte complex formation using alginate and chitosan, Carbohydrate polymers 74 (2008) 813-821.

* cited by examiner

*Primary Examiner* — Robert A Wax
*Assistant Examiner* — Melissa Mercier
(74) *Attorney, Agent, or Firm* — Mark Kertz

(57) ABSTRACT

An injectable non-aqueous composition and a method of treating a vascular disease, the non-aqueous composition including: chitosan having a particle size of no greater than 50 µm; alginate having a particle size of no greater than 50 µm; and a non-aqueous carrier; wherein upon combination and injection into the vascular system of a subject, the composition causes a diseased portion of the vascular system to be absorbed into surrounding tissue.

20 Claims, No Drawings

INJECTABLE NON-AQUEOUS COMPOSITIONS AND METHODS OF TREATING VASCULAR DISEASE

RELATED APPLICATIONS

This application is a continuation of U.S. patent application Ser. No. 14/959,446, filed Dec. 4, 2015, now U.S. Pat. No. 9,655,842, the entire contents of which are hereby incorporated by reference herein.

TECHNICAL FIELD

The following disclosure relates to injectable compositions, and, more particularly, to injectable non-aqueous compositions and methods of treating vascular disease.

BACKGROUND

Varicose veins, such as spider veins, telangiectasias, reticular varicose veins, bulging varicose vein tributaries, and varicose saphenous veins, are not only cosmetically bothersome, but also can cause burning, stinging, itching, aching, edema, and can even lead to skin changes and ulcer formation, as well as debility. Systems and methods for treating vascular diseases, particularly varicose veins, are desired.

SUMMARY OF THE INVENTION

The present disclosure provides injectable non-aqueous compositions and methods of treating a vascular disease. Upon injection into a vessel of a patient's vasculature and contact with an aqueous component, such as blood, a non-aqueous composition of the present disclosure forms a gel that seals the vessel and prevents blood from flowing back into the treated area of the vessel, both during gelation and after gelation.

In general, in one aspect, the implementation of the disclosure features a non-aqueous composition that includes: chitosan having a particle size of no greater than 50 µm; alginate having a particle size of no greater than 50 µm; and a non-aqueous carrier; wherein upon combination and injection into the vascular system of a subject, the chitosan and alginate form a polyelectrolyte gel in situ.

Upon injection in the vascular system of a subject and contacting blood, the chitosan and alginate precipitate and form a gel. In certain embodiments, prior to injection at the desired site of the vascular system of a subject, the non-aqueous composition is in at least two parts, wherein the chitosan is in one part and the alginate is in a separate part.

One or more of the following features may be included in compositions of the present disclosure.

In one aspect, a non-aqueous composition may include a gel tuning agent. In one aspect, the gel tuning agent may include a crosslinker, a gelling agent, a plasticizer, a binder, or a combination thereof. In one aspect, the gel tuning agent may include a crosslinker selected from the group of an aldehyde, a phosphate, an epoxide, an isocyanate, a natural crosslinker, an NHS-functionalized polyether, a gluconate salt, and a combination thereof. In one aspect, the gel tuning agent may include a plasticizer selected from the group of an alkyl citrate, an adipate, a triglyceride, and a combination thereof. In one aspect, the gel tuning agent may include a gelling agent selected from the group of a polyol, a polysaccharide, a polar aprotic solvent, an oil, and a combination thereof. In one aspect, the gel tuning agent may include a binder.

In one aspect of a non-aqueous composition of the present disclosure, the non-aqueous carrier may include a polyether, an ester, a glycerolipid, or a combination thereof.

In one aspect of a non-aqueous composition of the present disclosure, the non-aqueous composition may be a two-part composition, wherein the chitosan and alginate are in separate parts.

In one aspect of a non-aqueous composition of the present disclosure, the chitosan and alginate are each present in an amount of 1-5 wt-%.

In general, in one aspect, the implementation of the disclosure involves a method of treating a vascular disease. The method includes: providing a non-aqueous composition that includes: chitosan having a particle size of no greater than 50 µm; alginate having a particle size of no greater than 50 µm; and a non-aqueous carrier; and injecting the non-aqueous composition into the vascular system of a subject to form in situ a vascular embolism comprising a chitosan-alginate polyelectrolyte gel.

One or more of the following features may be included in methods of the present disclosure.

In one aspect, a method of the present disclosure involves the use of a non-aqueous composition that may include a gel tuning agent. In one aspect, the gel tuning agent may include a crosslinker, a gelling agent, a plasticizer, a binder, or a combination thereof. In one aspect, the gel tuning agent may include a crosslinker selected from the group of an aldehyde, a phosphate, an epoxide, an isocyanate, a natural crosslinker, an NHS-functionalized polyether, a gluconate salt, and a combination thereof. In one aspect, the gel tuning agent may include a plasticizer selected from the group of an alkyl citrate, an adipate, a triglyceride, and a combination thereof. In one aspect, the gel tuning agent may include a gelling agent selected from the group of a polyol, a polysaccharide, a polar aprotic solvent, an oil, and a combination thereof. In one aspect, the gel tuning agent may include a binder.

In one aspect, a method of the present disclosure involves the use of a non-aqueous composition that includes a non-aqueous carrier that may include a polyether, an ester, a glycerolipid, or a combination thereof.

In one aspect, a method of the present disclosure involves the use of a non-aqueous composition that may be a two-part composition, wherein the chitosan and alginate are in separate parts.

In one aspect, a method of the present disclosure involves the use of a non-aqueous composition wherein the chitosan and alginate are each present in an amount of 1-5 wt-%.

The disclosure may be implemented to realize one or more of the following advantages. The non-aqueous compositions can occlude blood vessels which will be absorbed into surrounding tissue to treat varicose veins, such as spider veins. The non-aqueous compositions can be injected through a small gauge needle, such as a 30 G needle. The non-aqueous compositions can be modified to tune gelation time. The non-aqueous compositions do not stain the skin of the patient. The non-aqueous compositions do not feel hard under the patient's skin.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples may be used in various combinations. In each instance, the recited list serves only as a representative group and should not be interpreted as an exclusive list.

DETAILED DESCRIPTION OF ILLUSTRATIVE EMBODIMENTS

The present disclosure provides an injectable non-aqueous composition and a method of treating a vascular disease, particularly varicose veins. Such composition and method include a polyelectrolyte gel formed in situ. Such gels are hemostatic and result in clotting of blood where injected in the target vessel (e.g., a spider vein).

Vascular diseases that may benefit from use of the injectable composition described herein include, for example, varicose veins (such as spider veins, telangiectasias, reticular varicose veins, bulging varicose vein tributaries, and varicose saphenous veins), arteriovenous malformations (AVMs), aneurysms, Varicocele, Portal Vein, etc.

The non-aqueous composition includes chitosan and alginate. Chitosans are a family of deacetylated derivatives of chitin, a natural polysaccharide. Chitosans may have different degrees of deacetylation and molecular weights. A chitosan is a linear polysaccharide composed of randomly distributed β-(1-4)-linked D-glucosamine (deacetylated unit) and N-acetyl-D-glucosamine (acetylated unit) of the following structure:

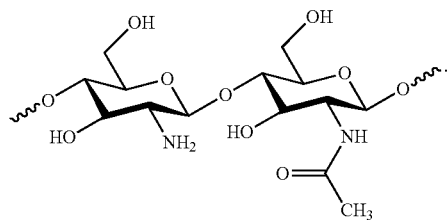

The degree of deacetylation (% DA), which can be determined by NMR spectroscopy, in commercial chitosans is typically 60% to 100%, or 70% to 95%. The weight average molecular weight, which can be determined by size exclusion chromatography with light scattering detection, of commercially available chitosans is typically about 10 kDa to about 1000 kDa. A preferred chitosan has a molecular weight about 50 kDa to about 600 kDa with a degree of deacetylation range of 75% to 95%. Water-soluble chitosan can be obtained commercially from FMC BioPolymer under the trade name PROTASAN (Chitosan Chloride and Chitosan Glutamate salts) in a powdered form in a very small particle size (e.g., no greater than 50 µm).

Alginates are a family of naturally occurring anionic polysaccharides. An alginate includes homopolymeric blocks of (1-4)-linked β-D-mannuronate (M) and its C-5 epimer α-L-guluronate (G) residues, respectively, covalently linked together in different sequences or blocks. The monomers can appear in homopolymeric blocks of consecutive G-residues (G-blocks), consecutive M-residues (M-blocks), or alternating M and G-residues (MG-blocks). An exemplary structure is as follows:

The weight average molecular weight, which can be determined by size exclusion chromatography with light scattering detection, of commercially available alginates is typically about 10 kDa to about 1000 kDa. A preferred alginate has a molecular weight in the range of about 50 kDa to about 600 kDa. Alginate can be obtained commercially from FMC BioPolymer under the trade name PRONOVA in a powdered form in a very small particle size (e.g., no greater than 50 µm).

In one exemplary embodiment, a non-aqueous composition includes: a chitosan having a particle size of no greater than 50 µm; an alginate having a particle size of no greater than 50 µm; and a non-aqueous carrier; wherein upon combination and injection into the vascular system of a subject, the chitosan and alginate form a polyelectrolyte gel in situ. The non-aqueous carrier may be any of the non-aqueous carriers described below.

A gel forms upon the transition from a non-aqueous powder suspension to a hydrated viscous matrix. Upon injection in the vascular system of a subject and contacting blood, the chitosan and alginate precipitate and form a gel. This gel includes a polyelectrolyte complex formed by the electrostatic interaction of the cationic amino groups of the chitosan and anionic carboxylate groups of the alginate.

In certain embodiments, prior to injection at the desired site of the vascular system of a subject, the non-aqueous composition may be in one part (e.g., a suspension in container such as a vial or syringe sealed with an inert atmosphere), or it may be in at least two parts, wherein the chitosan is in one part and the alginate is in a separate part (each of which may be sealed in an inert atmosphere in a container such as a vial or syringe). If the composition is in multiple parts, a medical practitioner combines the various parts prior to use.

In one exemplary embodiment, a method of treating a vascular disease includes: providing a non-aqueous composition that includes: a chitosan having a particle size of no greater than 50 µm (micrometers or microns); an alginate having a particle size of no greater than 50 µm; and a non-aqueous carrier; and injecting the non-aqueous composition into the vascular system of a subject to form in situ a vascular embolism including a chitosan-alginate polyelectrolyte gel.

In certain embodiments, the injecting occurs through the use of a small gauge needle. For example, a 30 gauge needle (i.e., 30 G needle with approximately 300 µm in diameter) is typically used for injecting the non-aqueous composition into spider veins.

In certain embodiments, the chitosan and alginate are present in the composition (in one or more parts) in a molar ratio of about 25:75 to about 75:25, or in other embodiments

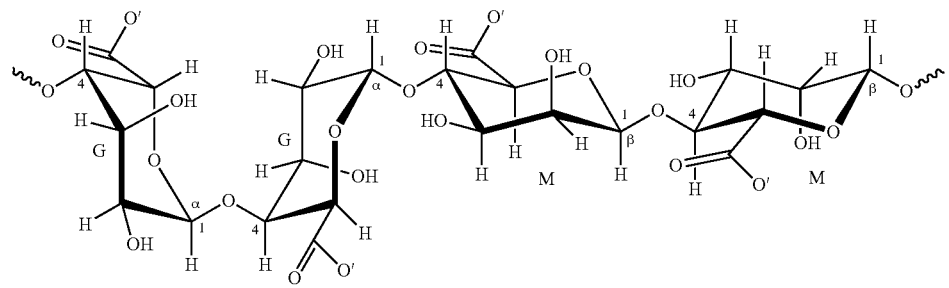

in a molar ratio of about 40:60 to about 60:40, or in still other embodiments in a molar ratio of about 50:50.

In an exemplary composition of the present disclosure, one or more chitosans can be used if desired. In certain embodiments, such as those requiring injectability through a small gauge needle (e.g., 30 G) the total amount of chitosan(s) can be at least 1 weight percent (wt-%), or at least 2 wt-%, or at least 3 wt-%, or at least 4 wt-%, or at least 5 wt-%, based on the total weight of all components of the composition (whether in one part or more than one part). In other embodiments, the total amount of chitosan(s) may be up to 20 wt-%, or up to 10 wt-%, or up to 5 wt-%, based on the total weight of all components of the composition (whether in one part or more than one part).

In an exemplary composition of the present disclosure, one or more alginates can be used if desired. In certain embodiments, such as those requiring injectability through a small gauge needle (e.g., 30 G), the total amount of alginate(s) can be at least 1 weight percent (wt-%), or at least 2 wt-%, or at least 3 wt-%, or at least 4 wt-%, or at least 5 wt-%, based on the total weight of all components of the composition (whether in one part or more than one part). In other embodiments, the total amount of alginates(s) may be up to 20 wt-%, or up to 10 wt-%, or up to 5 wt-%, based on the total weight of all components of the composition (whether in one part or more than one part).

One or more non-aqueous liquids can be used as the non-aqueous carrier. Such non-aqueous liquids may be inert carriers ("inert" in this context meaning that they do not interact in the gelling process) or they may be non-aqueous liquids that function as gel tuning agents as described below.

In certain embodiments, the non-aqueous carrier includes a polyether, an ester (such as dibutyl sebacate, tributyl citrate, acetyl tributyl citrate, dibutyl phthalate, etc.), a glycerolipid (such as triacetin, etc.), or a combination thereof. Exemplary polyethers suitable for use as a non-aqueous carrier include polyethylene glycol having a molecular weight of no more than about 400 Daltons, or no more than about 300 Daltons, or no more than about 200 Daltons, One or more non-aqueous carriers can be used if desired. In certain embodiments, the total amount of non-aqueous carrier(s) can be at least 50 wt-%, or at least 60 wt-%, or at least 70 wt-%, or at least 80 wt-%, or at least 90 wt-%, based on the total weight of all components of the composition (whether in one part or more than one part). In certain embodiments, the total amount of non-aqueous carrier(s) can be up to 98 wt-%, based on the total weight of all components of the composition (whether in one part or more than one part).

In certain embodiments, the non-aqueous composition further includes a gel tuning agent (which may be incorporated in one or more parts, if the non-aqueous composition is in the form of more than one part). Herein, a gel tuning agent is a material that enables a practitioner to tune the initiation of precipitation, as well as the kinetics of gel formation. Thus, selection of one or more gel tuning agents can provide better control of gelation upon injection.

The initiation of precipitation, i.e., the time after injection that the components begin to precipitate, depends on the particular application and desired result. In certain embodiments, the initiation of precipitation occurs instantaneously, or in at least 0.1 minute, or at least 2 minutes, or at least 5 minutes, or at least 10 minutes, after contact of the combination of chitosan and alginate in an aqueous-based liquid (e.g., blood). In certain embodiments, the initiation of precipitation occurs in no more than 0.1 minute, or no more than 2 minutes, or no more than 5 minutes, or no more than 10 minutes, after contact of the combination of chitosan and alginate in an aqueous-based liquid (e.g., blood).

The time for gel formation depends on the particular application and desired result. In certain embodiments, gel formation occurs in at least 1 minute, or at least 2 minutes, or at least 3 minutes, or at least 4 minutes, or at least 5 minutes, after contact of the combination of chitosan and alginate in an aqueous-based liquid (e.g., blood). In certain embodiments, gel formation occurs in up to 60 minutes, or up to 50 minutes, or up to 40 minutes, or up to 30 minutes, or up to 10 minutes, or up to 1 minute, after contact of the combination of chitosan and alginate in an aqueous-based liquid (e.g., blood).

In certain embodiments, the total amount of gel tuning agent(s) can be at least 2.5 wt-%, based on the total weight of all components of the composition (whether in one part or more than one part). In certain embodiments, the total amount of gel tuning agent(s) can be up to 50 wt-%, or up to 40 wt-%, or up to 30 wt-%, or up to 20 wt-%, or up to 10 wt-%, based on the total weight of all components of the composition (whether in one part or more than one part).

In certain embodiments the gel tuning agent includes a crosslinker, a gelling agent, a plasticizer, a binder, or a combination thereof.

In certain exemplary embodiments, the gel tuning agent is a crosslinker selected from the group of an aldehyde, a phosphate, an epoxide, an isocyanate, a natural crosslinker, an NHS-functionalized polyether, a gluconate salt, and a combination thereof. Exemplary aldehydes suitable for use as a gel tuning agent include glutaraldehyde, formaldehyde, and aldehyde functionalized polyethylene glycol. Exemplary phosphates suitable for use as a gel tuning agent include tripolyphosphate and beta-glycerophosphate. Exemplary epoxides suitable for use as a gel tuning agent include poly(ethylene glycol) and diglycidyl ether. Exemplary isocyanates include polyethylene glycol isocyanate and 6-hexamethylene diisocyanate. Exemplary natural crosslinkers include genipin, dopamine, and transglutaminases. Exemplary NHS-functionalized polyethers include NHS-ester functionalized polyethylene glycol (N-hydroxyl succinimide (NHS), functionalized methoxyl polyethylene glycol (mPEG-NHS)) having a molecular weight of no more than about 20 kDa. Exemplary gluconate salts include calcium D gluconate.

In certain embodiments, the gel tuning agent is a plasticizer selected from the group of an alkyl citrate, an adipate, a triglyceride, and a combination thereof. Exemplary alkyl citrates suitable for use as a gel tuning agent include triethyl citrate (TEC), acetyl triethyl citrate (ATEC), tributyl citrate (TBC), and acetyl tributyl citrate (ATBC). Exemplary adipates suitable for use as a gel tuning agent include dibutyl sebacate (DBS). Exemplary triglycerides suitable for use as a gel tuning agent include triacetin (i.e., glycerin triacetate or 1,2,3-triacetoxypropme).

In certain embodiments, the gel tuning agent is a gelling agent selected from the group of a polyol, a polysaccharide, a polar aprotic solvent, an oil, and a combination thereof. Exemplary polyols suitable for use as a gel tuning agent include glycerol, 1,3-propanediol, and 1,2-propanediol. Exemplary polysaccharides suitable for use as a gel tuning agent include trehalose, mannose, and galatose. Exemplary polar aprotic solvents suitable for use as a gel tuning agent include dimethyl sulfoxide (DMSO). Exemplary oils include sesame oil and corn oil.

In certain embodiments, the gel tuning agent is a binder. An exemplary binder is a glycerol fatty acid ester. Exemplary glycerol fatty acid esters suitable for use as a gel tuning agent include glyceryl monooleate, sorbitol monooleate, glyceryl monostearate, and similar long and medium chain triglycerides.

In various examples described below, the alginate used was PRONOVA UP LVM (approximate MW 75 kDa to 200 kDa) and chitosan used was PROTASAN UP CL 113 (approximate MW less than 200 kDa) (FMC Novamatrix, Sweden). Exemplary non-aqueous compositions include the following that form a precipitate instantly upon injection into water, and form a gel within 5 minutes:

(1) 2.5% Alginate (PRONOVA, FMC), 2.5% Chitosan (PROTASAN, FMC), 5% GMO (Glyceryl Monooleate, Croda) binder, 25% Glycerol gelling agent, 65% PEG-200 (Polyethylene Glycol 200 MW) non-aqueous carrier;

(2) 2.5% Alginate (PRONOVA, FMC), 2.5% Chitosan (PROTASAN, FMC), 5% Sesame Oil (Croda), 25% Glycerol gelling agent, 65% PEG-200 (Polyethylene Glycol 200 MW) non-aqueous carrier;

(3) 2.5% Alginate (PRONOVA, FMC), 2.5% Chitosan (PROTASAN, FMC), 10% Glycerol, 25% Sesame Oil (Croda), 60% PEG-200 (Polyethylene Glycol 200 MW) non-aqueous carrier; and (4) 5% Alginate (PRONOVA, FMC), 5% Chitosan, 25% Glycerol gelling agent, 65% PEG-200 (Polyethylene Glycol 200 MW) non-aqueous carrier.

Exemplary non-aqueous compositions also include the following that form a gel within 20 minutes:

(5) 5% Alginate (PRONOVA, FMC), 5% Chitosan (PROTASAN, FMC), 40% Tributyl citrate (Sigma) plasticizer/non-aqueous carrier, 50% PEG-300 (Polyethylene Glycol 300 MW) non-aqueous carrier;

(6) 5% Alginate (PRONOVA, FMC), 5% Chitosan (PROTASAN, FMC), 50% Triacetin (Sigma) plasticizer/non-aqueous carrier, 40% PEG-300 (Polyethylene Glycol 300 MW) non-aqueous carrier;

(7) 5% Alginate (PRONOVA, FMC), 5% Chitosan (PROTASAN, FMC), 5% Triethyl citrate (Sigma) plasticizer, 85% Triacetin plasticizer/non-aqueous carrier; and (8) 2.5% Alginate (PRONOVA, FMC), 2.5% Chitosan (PROTASAN, FMC), 5% Dibutyl sebacate (Sigma) plasticizer/non-aqueous carrier, 65% Triacetin plasticizer/non-aqueous carrier, 25% Glycerol gelling agent.

The chitosan and alginate may settle/separate in the syringe or vial over time. In such instances, it is preferable to have at least the non-aqueous carrier(s) in the second syringe or vial to enable the practitioner to mix the non-aqueous carrier(s) with the non-aqueous composition to create a uniform suspension. The examples below describe such method of use.

Delivery Example 1—Single or Multiple Syringes

The compositions may be provided in a single prefilled syringe, or multiple pre-filled syringes, having chitosan, alginate, one or more non-aqueous carriers, and one or more optional gel tuning agents. For the treatment of spider veins, the suspension and/or non-aqueous carrier may be provided in a pre-filled 1 mL, 3 mL, 5 mL, or 10 mL syringe. Another syringe may be provided with a non-aqueous carrier(s). The non-aqueous carrier(s) in the second syringe may be the same non-aqueous carrier(s) as in the first syringe, or may be a different non-aqueous carrier(s). The practitioner may connect the two syringes with a luer connector and mix the contents 5-10 times to create a uniform suspension prior to injecting into the target vessel (treatment).

Delivery Example 2—Single or Multiple Vials

The compositions may be provided in a single vial, or in multiple vials, having chitosan, alginate, non-aqueous carrier and gel tuning agent in one or both vials. The contents of the vials will be mixed on a vortex mixer to create a uniform suspension and then aspirated into one or more syringes. The syringes may then be combined or used as-is as described in Delivery Example 1.

Delivery Example 3—Dual Barrel Syringes

The compositions may be provided in a dual barrel syringe. A first barrel may include chitosan, alginate, one or more non-aqueous carriers, and one or more optional gel tuning agents. A second barrel may include one or more of the non-aqueous carriers. The non-aqueous carrier(s) in the second barrel may be the same non-aqueous carrier(s) as in the first barrel, or may be a different non-aqueous carrier(s). The practitioner may connect a mixing element at the end of the first and second barrels to create a uniform suspension prior to treatment. In other embodiments, the mixing element is already attached, or is an integral part of, the dual barrel syringe. The non-aqueous composition may be delivered via a needle as small as a 30 G size or a catheter up to 9 F in size.

EXAMPLES

Objects and advantages of this invention are further illustrated by the following examples, but the particular materials and amounts thereof recited in these examples, as well as other conditions and details, should not be construed to unduly limit this invention. These examples are merely for illustrative purposes only and are not meant to be limiting on the scope of the appended claims.

Materials and Methods

Alginate (Ultrapure PRONOVA Sodium Alginates, LVM) and Chitosan (PROTASAN UP CL 113) were purchased from Novamatrix (FMC, Sweden). Glycerol Monooleate, PEG-200, PEG-300, and Sesame Oil were purchased from Croda Inc (Edison, N.J.). Triacetin, Tributyl Citrate, Glycerol, and Dimethyl Sulfoxide were purchased from Sigma Aldrich (St Louis, Mo.).

Particle Size Measurements

Suspensions of chitosan and alginate for determination of particle size were prepared as follows. A 0.02% weight per volume suspension of each material was prepared in triacetin (i.e., glycerin triacetate or 1,2,3-triacetoxypropane). The suspension was vortexed for 5 minutes immediately prior to measurement. A baseline particle count in the vehicle (Triacetin) was also performed and reported. Particle counts were measured in a HIAC 9703 Liquid Particle Counting System with an HRLD 150 Sensor (Beckman Coulter Life Sciences, Brea, Calif.). Briefly, 2 milliliters (mL) of the diluted suspension in Triacetin was sampled each time and particle sizes in the range of 1.3 microns to 100 microns. The particle sizes are determined by the method of light obscuration and the results are displayed based on particles/mL for various size ranges up to 100 microns. For both Alginate and Chitosan, 95% of the particles had a size less than 50 microns.

Preparation of Compositions

To prepare non-aqueous compositions, a 5-mL (milliliter) or 10-mL glass vial was used to combine chemical combinations as mentioned in Table 1. Known masses of the chemicals were added using a balance with a precision of 0.1 mg (milligram) for a total mass of 2000 mg. The glass vial was sealed with a rubber cap and crimp and placed on a vortex mixer for 10 minutes prior to testing the non-aqueous compositions. In instances where the non-aqueous composition was not intended to be used immediately, the glass vial and ingredients were purged, combined, and sealed under nitrogen or argon in a glove box.

TABLE 1

Non-aqueous compositions (all weights in mg)

| Alginate | Chitosan | Glycerol | Glycerol Monooleate | PEG-300 | Triacetin | Tributyl Citrate | Dimethyl Sulfoxide | Sesame Oil | PEG-200 |
|---|---|---|---|---|---|---|---|---|---|
| 50 | 50 | 500 |  | 1400 |  |  |  |  |  |
| 50 | 50 |  |  | 1900 |  |  |  |  |  |
| 50 | 50 | 200 |  |  | 1700 |  |  |  |  |
| 50 | 50 |  |  | 900 | 900 |  |  |  |  |
| 50 | 50 | 500 | 100 | 1300 |  |  |  |  |  |
| 50 | 50 | 200 | 200 | 1300 | 200 |  |  |  |  |
| 50 | 50 |  |  |  |  | 1900 |  |  |  |
| 50 | 50 |  |  | 1900 |  |  |  |  |  |
| 50 | 50 |  |  | 400 | 1000 |  | 500 |  |  |
| 50 | 50 | 400 |  | 1500 |  |  |  |  |  |
| 10 | 10 | 100 | 100 |  |  |  |  | 80 | 700 |
| 20 | 20 | 100 | 100 |  |  |  |  | 60 | 700 |
| 50 | 50 | 500 | 100 |  |  |  |  |  | 1300 |

Gel Formation In-Vitro

The non-aqueous compositions were mixed using a vortex apparatus for 5 minutes prior to use as mentioned previously. The non-aqueous composition was drawn into 1 mL syringe and a 30 G (gauge) needle was attached at the tip. The non-aqueous composition was injected into a phosphate buffered saline solution, human blood plasma (citrated), or ovine blood (citrated) and the kinetics of gel formation were observed. In all instances, non-aqueous composition formed cohesive gels within 1-20 minutes and were all injectable using a 30 G needle.

Gel Formation In-Vivo

One example of use of a non-aqueous composition for long-term occlusion, complete vein closure, and vein resolution of the rabbit ear marginal vein is described. Female New Zealand white rabbit was used and acclimatized for 10 days prior to procedure. On Day 10, the rabbits were prepared in a sterile operating room with ears shaven. A digital pre-treatment image of the ear was captured. A test non-aqueous composition was prepared as described above with composition (w/w): 2.5% Alginate, 2.5% Chitosan, 5% Glyceryl Monooleate, 25% Glycerol, and 65% PEG-200. The non-aqueous composition was aspirated into a 1 mL syringe and a 30 G needle was attached at the tip. The non-aqueous composition was injected into the marginal vein of the rabbit ear such that approximately 5 centimeters (cm) of the vessel length was treated with the non-aqueous composition.

Immediate gel formation was observed with clot formation in the areas around the non-aqueous composition. The vessel remained occluded at weekly follow-up and was fully absorbed into surrounding tissue by day 70. The animal was sacrificed at day 70 and the ear preserved in 10% Neutral buffered formalin for histological analysis. Transverse sections of the vein were obtained at 4 locations along the treatment length as indicated. The sections were stained for H&E (Hematoxylin and Eosin), Prussian Blue, and Gomori Trichrome. Results showed formation of collagen in the area where the vein was originally present, with limited red blood cell pooling (no hemosiderin) and no vessel wall present (Elastic Trichrome).

The complete disclosures of the patents, patent documents, and publications cited herein are incorporated by reference in their entirety as if each were individually incorporated. Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed is:

1. A method of treating a vascular disease, the method comprising:
   providing a non-aqueous composition comprising:
      a chitosan having a particle size of no greater than 50 µm;
      an alginate having a particle size of no greater than 50 µm; and
      a non-aqueous carrier; and
   injecting the non-aqueous composition into a diseased portion of a vascular system of a subject to cause the diseased portion to be absorbed into surrounding tissue.

2. The method of claim 1 wherein the diseased portion comprises an aneurysm.

3. The method of claim 1 wherein injecting the non-aqueous composition comprises forming an embolism in the diseased portion.

4. The method of claim 3 wherein the diseased portion comprises an aneurysm.

5. The method of claim 3 wherein the embolism comprises a chitosan-alginate polyelectrolyte gel.

6. The method of claim 1 wherein the non-aqueous composition further comprises a gel tuning agent.

7. The method of claim 6 wherein the gel tuning agent comprises a crosslinker, a gelling agent, a plasticizer, a binder, or a combination thereof.

8. The method of claim 6 wherein the gel tuning agent comprises a crosslinker selected from the group of an aldehyde, a phosphate, an epoxide, an isocyanate, a natural crosslinker, an NHS-functionalized polyether, a salt, and a combination thereof.

9. The method of claim 6 wherein the gel tuning agent comprises a gelling agent selected from the group of a polyol, a polysaccharide, a polar aprotic solvent, an oil, and a combination thereof.

10. The method of claim 6 wherein the gel tuning agent comprises a plasticizer selected from the group of an alkyl citrate, an adipate, a triglyceride, and a combination thereof.

11. The method of claim 6 wherein the gel tuning agent comprises a binder.

12. The method of claim 1 wherein the non-aqueous carrier comprises a polyether, an ester, a glycerolipid, or a combination thereof.

13. The method of claim 1 wherein the non-aqueous composition is a two-part composition, wherein the chitosan and alginate are in separate parts.

14. The method of claim 1 wherein the chitosan and alginate are each present in the composition in an amount of 1-5 wt-%.

15. A method of treating a vascular disease, the method comprising:
   providing a non-aqueous composition comprising:
      a chitosan having a particle size of no greater than 50 µm;
      an alginate having a particle size of no greater than 50 µm; and
      a non-aqueous carrier; and
   injecting the non-aqueous composition into a diseased portion of a vascular system of a subject to form in situ a chitosan-alginate polyelectrolyte gel.

16. The method of claim 15 wherein the diseased portion comprises an aneurysm.

17. The method of claim 15 wherein injecting the non-aqueous composition comprises forming an embolism in the diseased portion.

18. The method of claim 17 wherein the diseased portion comprises an aneurysm.

19. The method of claim 15 wherein the non-aqueous composition further comprises a gel tuning agent.

20. The method of claim 19 wherein the gel tuning agent comprises a crosslinker, a gelling agent, a plasticizer, a binder, or a combination thereof.

* * * * *